(12) United States Patent
Canaday (10) Patent No.: US 10,179,220 B2
(45) Date of Patent: Jan. 15, 2019

(54) ANIMAL RESPIRATORY TREATMENT MASKS AND SYSTEM

(71) Applicant: Rebecca G. Canaday, Fort Scott, KS (US)

(72) Inventor: Rebecca G. Canaday, Fort Scott, KS (US)

(*) Notice: Subject to any disclaimer, the term of this patent is extended or adjusted under 35 U.S.C. 154(b) by 154 days.

(21) Appl. No.: 14/999,989

(22) Filed: Jul. 22, 2016

(65) Prior Publication Data

US 2017/0035981 A1    Feb. 9, 2017

Related U.S. Application Data

(60) Provisional application No. 62/282,649, filed on Aug. 6, 2015.

(51) Int. Cl.
| | |
|---|---|
| *A61M 16/00* | (2006.01) |
| *A61M 16/06* | (2006.01) |
| *A61M 16/16* | (2006.01) |
| *A61M 16/08* | (2006.01) |
| *A61M 16/10* | (2006.01) |

(52) U.S. Cl.
CPC ........ *A61M 16/0683* (2013.01); *A61M 16/16* (2013.01); *A61M 16/0063* (2014.02); *A61M 16/0875* (2013.01); *A61M 16/101* (2014.02); *A61M 2250/00* (2013.01)

(58) Field of Classification Search
CPC .............. A61M 16/0683; A61M 16/18; A61M 2250/00
See application file for complete search history.

(56) References Cited

U.S. PATENT DOCUMENTS

| | | | | |
|---|---|---|---|---|
| 3,915,165 | A * | 10/1975 | Rambosek | A61D 7/00 128/201.11 |
| 4,002,167 | A * | 1/1977 | Rambosek | A61D 7/04 128/206.24 |
| 4,722,334 | A * | 2/1988 | Blackmer | A61D 7/04 128/203.16 |
| 4,953,546 | A * | 9/1990 | Blackmer | A61D 7/04 128/203.16 |
| 4,955,372 | A * | 9/1990 | Blackmer | A61D 7/04 128/203.16 |
| 7,111,626 | B2 * | 9/2006 | Schmehl | A61D 7/04 128/200.23 |
| D753,352 | S | 4/2016 | Collins | |
| 2003/0070678 | A1 * | 4/2003 | Wartman | A61M 16/0045 128/203.14 |
| 2010/0043798 | A1 * | 2/2010 | Sullivan | A61M 16/06 128/205.25 |
| 2011/0270085 | A1 * | 11/2011 | King | A62B 27/00 600/439 |
| 2012/0203125 | A1 * | 8/2012 | Moran | A61D 7/04 600/532 |
| 2016/0361510 | A1 * | 12/2016 | Alphonse | A61M 16/06 |

* cited by examiner

*Primary Examiner* — Kristen Matter
(74) *Attorney, Agent, or Firm* — John H. Miller (57) ABSTRACT

The invention involves masks and systems for providing respiratory treatments to various animals including horses, mules and ponies. The masks are low in cost due to simple designs, a very low thickness requiring less material and the systems include the masks of the invention.

7 Claims, 12 Drawing Sheets

Section B-B

Figure 14

ANIMAL RESPIRATORY TREATMENT MASKS AND SYSTEM

This application claims the benefit of Provisional Patent Application No. 62/282,649 filed on Aug. 6, 2015.

The invention pertains to low cost respiratory treatment mask devices for large animals particularly equine animals including horses, mules, ponies and also cattle, especially show cattle and other farm or zoo animals including camels, llamas, alpakas and others. The invention also pertains to methods of using the device to provide respiratory treatment for animals.

BACKGROUND

It is known to give equine animals like horses and cattle, particularly show horses, cattle, and other show, income producing and zoo animals respiratory treatments when they show symptoms of respiratory distress. Animals like horses, mules, burros, cattle and other animals are under a lot of stress when they are hauled to shows, rodeos, etc., and stress and change of climate can bring on the respiratory issues. One or more respiratory devices are known for horses but they add stress to the animal and/or very expensive. For example, one or more of such devices does not allow air into the mask when it is first put onto the animal causing some panic with the animal until air or oxygen is forced into the mask with a pump. One of the masks has a snug fitting gasket that presses against the animal's cheeks causing some stress before and during treatment. Also, competitive masks have walls so thick that the weight of the masks, without securement straps, exceed one pound (454 grams) by a few to several ounces, e.g. by 2-8 ounces (56-226 grams), and because of the thick walls, e.g. 0.094 inch (about 2.35 mm) the transparency of the walls of the mask is poor. What is needed is a low cost device that is comfortable on the animals and does not cause them additional stress.

SUMMARY OF THE INVENTION

The invention includes low cost devices, such as animal nose masks for easily and quickly giving respiratory treatment to such animals as described above. The devices comprise loose fitting, low cost masks with an open top and having on its bottom end an opening with an external fitting for attachement to a hose, and another opening for allowing drainage and air into the mask at desired times. Attached to the masks in any suitable manner, preferably to its upper end close to the open end are one or more straps for wrapping around the top of the animal's head and/or neck to retain the mask onto the animal in the desired position for respiratory treatment. The strap or straps have along the length of at least one strap a securement device such as a buckle or material, preferably velcro strips for quick and easy securement and opening.

The masks are sufficiently inexpensive to make to allow such a low price, e.g. as little as less than one-fifth the price of one or more other respiratory masks on the market. The low price allows them to be disposable, but the mask can also be easily sterilized and used over and over. It's relatively low cost makes it practical in many instances to have a separate mask for each horse or animal, further insuring against spreading of disease from animal to animal. The low cost is due to the relatively small thickness of a major portion of the masks, the relatively low cost of the thermoplastic materials used in the masks, preferably relatively low softening point materials, and the economics of the methods of forming the masks, which methods are known for forming bottles, bowls and many other items. The mask, because of the material used to make the mask and its very low thickness, thinness is transparent or transparent enough to allow one to see the animals nose and mouth to position the mask in the desired position with respect to the inside bottom of the mask.

The major portion of the masks, i. e. the vertical portion, including an optional a top edge flared portion extending down no more than about 2 centimeters, preferably a distance of no more than 1.5, 1.25, 1, 0.75, 0.5, or 0.25 centimeters. At least 20 or 25 or 35 or 50 or 75 percent or more of the bottom wall of the mask has a thickness of less than about 1.55 millimeters, preferably less than about 1.1 millimeters or less than about 0.8 millimeters and as low as about 0.5 millimeters. The most preferred thickness of the major portion of the mask is in the range of about 0.7 to about 0.8 millimeters, more preferably about 0.635 mm or 0.75 mm to about 0.78 millimeters.

While the masks can have one or more corners where two planes of the sides or bottom or drain or inlet fitting of the mask form angles ranging from 90 degrees plus/minus 20 degrees, preferably there are no angled corners between any of the planes of the masks. Instead, most preferably all of the major planes of the masks, the bottom, sides, front and back are joined with curved, radiused surfaces. For example, the front and back are curved surfaces that are integral with the two sides. Likewise, the bottom is joined to the front, back and two sides integrally with curved or radiused surfaces. Preferably the entirety of the drain opening is in the flat portion of the bottom wall. Thus, the preferred masks have either no crevices or angled joints on the inside to trap bacteria and thus are more easily sterilized, or a potential of up to eight joints or angles or have four or less crevices or angled joints. Also, preferably, the drain opening is flush with the bottom and extending outside with no angled joints or crevice. The treatment connection can be shaped and formed in the same manner as the drain, but preferably it has an additional circular, curved and/or angled joint at the outer circumference of the recess or flange for the treatment connection piece to affect easier and mosre thorough cleaning between uses.

Figure 7:
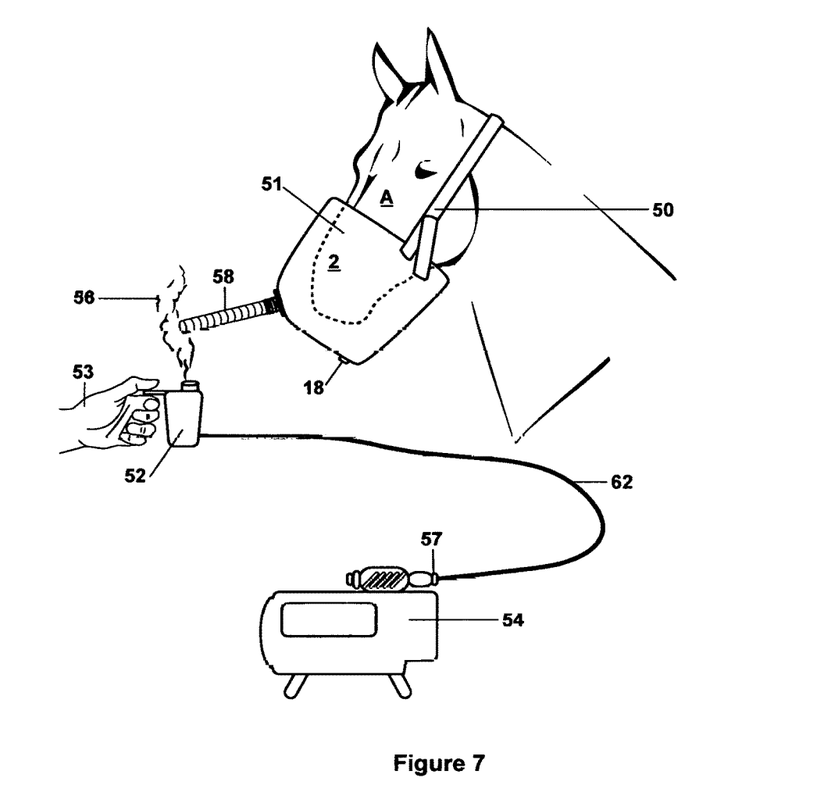
FIG. 7 is a perspective view of part of a horse's head with the mask properly positioned and with a flexible, corrugated tube attached to the medicinal inlet fitting of the mask, with a vapor coming from a medicine cup passing near an open end of the tube and a running compressor that is attached to the medicine cup with a tube of flowing air or gas causing the medicine to vaporize.

A connection piece, preferably fairly rigid tubular extension integral with the bottom of the mask, made from the same material as the mask or a different material, and having circumferential corrugations around the piece makes it easier to connect an air or gas tube (see 58 in FIGS. 7, 8, and 9) to the mask for feeding respiratory treatment vapor into the mask. Various medicinal respiratory treatment products are available on the market, e.g. collodial 0.9999 Pure Silver particles suspended in deionized water (10-14 PPM Ag) available from Silver Horse Care™ company at SILVERHORSECARE.com. The feed tubing, preferably, but not necessarily, is also circumferentially corrugated to make a secure fit such that when shakes his head, the feed tube will not disconnect which if it did, would scare most animals being treated, especially young animals like colts. The mask also preferably has a drain opening, preferably circular with a short tubular section extending below the outside bottom of the mask, to allow air into the mask, to allow any liquid in the mask to rapidly drain out and to allow excess vapor treatment of exit the bottom of the mask.

The masks are made using the various types of blow molding, vacuum molding and similar forming processes, and the materials used to make the masks are thermoplastic materials, preferably in sheet form, commonly used in such forming processes. Preferably, the material is a polymer or copolymer such as polyethylene, polypropylene, and other resins and polymers known for use in such processes, e.g. DuPont's Surlyn® 1652, 1706 and others. The respiratory mask 2 of the invention can be made with any polymer that can be blow molded, usually a thermoplastic polymer and is most preferably blow molded using a polymer of polyethylene and preferably high-density polyethylene. To reduce cost and produce practical transparency, the thickness of the walls and bottom of the mask are very thin, having a thickness in the range of 0.025 inch (0.63/4 mm) to 0.045 inch (1.143 mm) with a most preferred thickness being about 0.035 inch (0.9 mm). The thickness of the drain, and particularly the tubular extension 25 can be thicker to provide the strength and rigidity needed or desired.

The masks also have one or more straps, preferably attached at the upper edge portion of the masks, most preferably on each of the two sides of the mask. The strap(s) can be attached to the mask with stitching, staples, rivets or other known fastening devices, or preferably, the upper portion of each of the two sides of the mask will have a slot, with or without a pocket formed therein to allow the strap to be flush with the inside of the major portion of the mask, the slot allowing an end portion of the strap, or straps, to be pushed through the slot and pulled up to attach to the strap outside, above, the top of the mask using a snap, buckle or other securement device including velcro strip(s). One or more buckles, velcro strip(s), clips, etc. attached at appropriate locations on the strap or straps allow for adjustment to place the mask at the appropriate location on the animals head for treatment.

Most masks do not have any gasket at the top of the masks, but it is preferred to use a lightweight gasket at the top of masks for use on horse colts and other young animals. Any type of gasket to limit the gap between the top of the mask and the animal's lower head can be used, but a preferred low cost gasket is made from readily foam plastic pipe insulation available in hardware and home and garden stores.

To determine the size of the mask you measure several different types of animal's, e.g. a horse's nose. Performance horses include cutting horses, reigning horses, quarter horses, thoroughbreds, race-horses and draft horses. You want a little clearance all around the mask between the mask walls and the horses nose, mouth and face. The position of the strap on the mask helps position the mask on the horses nose. If the horse has a small nose it is better for the gap to be in the backside of the horses nose rather than the front. The length(s) of the straps help to raise and lower the mask for the best fit for the input of the mist into the horses nose. For use on other animals you repeat this procedure on each type of animal.

This mask provides other advantages in addition to its lower manufacturing cost including lighter weight making it less likely to scare the animal, safer to use, and low enough in cost to be more often disposable avoiding need to sterilize or avoiding spreading disease. Also, because of the material used to make the mask and its very low thickness, thinness, it is transparent or transparent enough to allow one to see the animals nose and mouth to position the mask in the desired position with respect to the inside bottom of the mask.

The method of using the masks comprises the following, but not necessarily in this order:
1) Prepare the respiratory medicine that is planned for use,
2) make sure any oxygen concentrator or other gas providing device is in place and ready to use,
3) place a respiratory mask of the invention over the mouth and nose of an animal and secure it in place with one or more straps, cords or ribbon, etc. extending from one or both sides of the mask, extending at least one strap over the head or neck of the animal and secure the strap(s) leaving a space of about one-half or three-fourth Inch to about one inch between the inside bottom of the mask and the bottom of the animals mouth or nose (this step is done slowly and gently to avoid unnecessarily scaring the animal, but first let the animal see and smell the mask while moving very slowly, then when the animal seems comfortable, proceed),
4) attach a tubing, preferably, but not necessarily, a corrugated tubing, to the medicine input spout, inlet fitting, on the mask,
5 a) when using an air compressor, attach a metal tubing, preferably a metal tubing having good to high heat absorption, heat capacity, heat transfer coefficient and ability to dissipate heat to the air compressor and attach the other end to the medicine cup. Air compressors tend to heat the air to uncomfortable temperatures and the metal tubing will cool the air to a comfortable temperature for the horse/animal. A particularly good tubing is at least a 5 inch long, such as a six inch, preferably a seven inch long braided stainless steel covered plastic or metal tubing with metal couplings on each end, such as a braided hose available from
5 b) turn on the oxygen concentrator, or other gas supply when one of these is used instead of an air compressor, making sure that a medicine vapor is coming from the medicine container,
6) place the mask on horse using the Velcro™ straps to hold the mask on the horse. Remember, it may be scary to your horse at first. Let the horse look at it, smell it and be patient. After your horse is comfortable with the mask proceed to the following steps.
7) attach the other end of the clear tubing or the metal tubing to the inflow (small) spout of a medicine cup such as the medicine cup that is included with a MEDLINE Industries Inc. VixOne™ Nebulizer kit, or a similar med cup.
8) attach the medicine container to the other end of the tubing previously attached to the mask,
9) treat, nebulize, the animal for the prescribed time period,
10) following treatment remove the mask and clean the mask by spraying with a disinfectant and then rinse clean.

Herein, when a range of number values is disclosed it is to be understood by those of ordinary skill in the appropriate art(s) that each numerical value in between the upper limit and the lower limit of the range is also disclosed, to at least 0.01 of a full number. Thus in a range of 1 to 10, this includes 2.04 to 10, 3.06 to 8 or 8.50, and so on. The addition of a new limitation in a claim previously stating from 2 to 7 changing it to from 3-7 or 4-6 would not introduce new matter whether those new ranges were specifically disclosed in the specification or not because of this explanation of the meaning of a disclosed broader range, such as 1-10. This meaning of a range is in keeping with the requirement in 35 USC 112 that the disclosure be concise.

Further, when the word "about" is used herein it is meant that the amount or condition it modifies can vary some beyond that stated so long as the advantages of the invention are realized. Practically, there is rarely the time or resources available to very precisely determine the limits of all the parameters of one's invention because to do so would require an effort far greater than can be justified at the time the invention is being developed to a commercial reality. The skilled artisan understands this and expects that the disclosed results of the invention might extend, at least somewhat, beyond one or more of the limits disclosed. Later, having the benefit of the inventors' disclosure and understanding the inventive concept and embodiments disclosed including the best mode known to the inventor, the inventor and others can, without inventive effort, explore beyond the limits disclosed to determine if the invention is realized beyond those limits and, when embodiments are found to be without any unexpected characteristics, those embodiments are within the meaning of the term "about" as used herein. It is not difficult for the artisan or others to determine whether such an embodiment is either as expected or, because of either a break in the continuity of results or one or more features that are significantly better than reported by the inventor, is surprising and thus an unobvious teaching leading to a further advance in the art.

DETAILED DESCRIPTION OF SOME EMBODIMENTS AND BEST MODE

Figure 1:
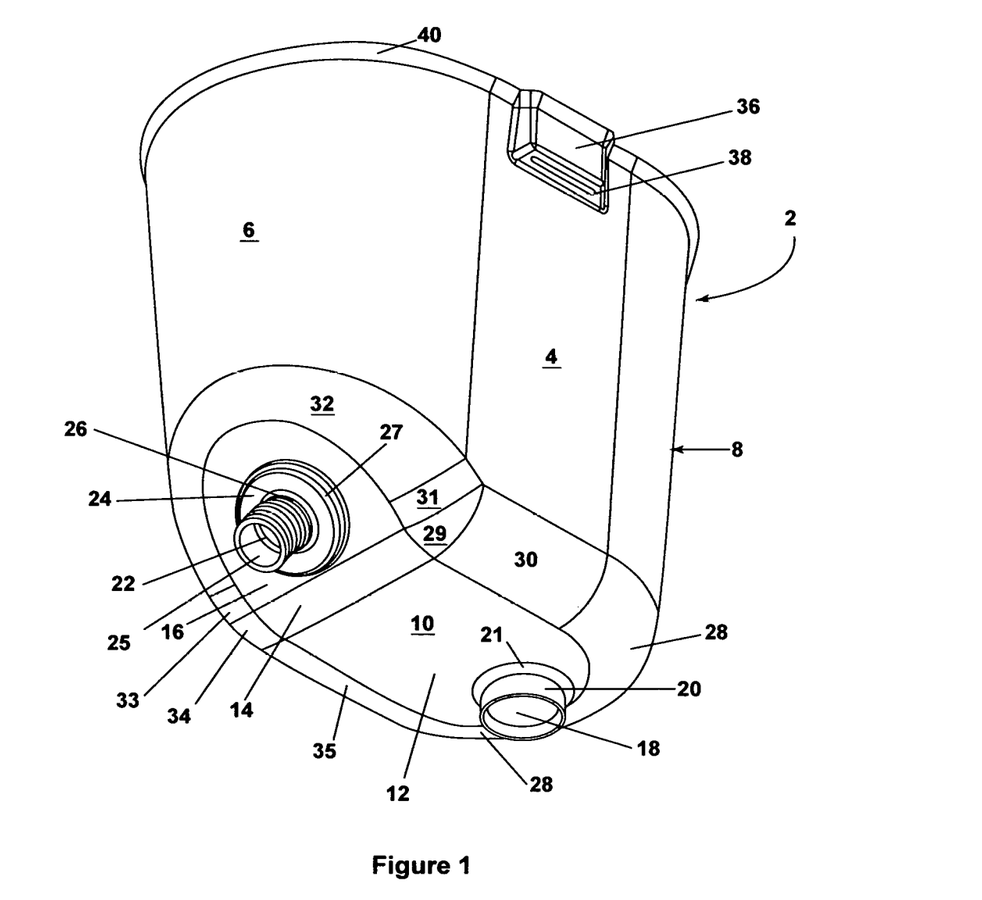
FIG. 1 is a perspective view of a respiratory mask according to the invention.

As shown in perspective view in FIG. 1, the invention comprises a respiratory animal mask 2 (hereafter mask) having two sides 4, 5 (not shown) a front face 6, preferably curved, a back face 8, preferably curved and a bottom 10, preferably flat. In the embodiment shown in FIG. 1, the bottom 10 has a a relatively flat section 12 integral with a curved section 14 that is integral with an angled section 16, the bottom 10 integral with the sides 4, 5 (not shown), the curved front 6 and the curved back 8, preferably with curved interfaces, 28, 29, 30 31, 32, 33, 34 and 35, between the bottom 10, the sides 4,5 and the front face 6 and the back face 8. The relatively flat section 12 of the bottom 10 has, near its rear or back end, a drain opening 18 surrounded with an optional fitting 20 integral with or attached to the relatively flat section 10 with a curved or radiused portion 21. The opening 18 is for the purpose of allowing air into the mask 2 and also to drain any liquid that collects in the lower portion of the mask 2 out of the mask 2. For a horse the interior diameter of the drain 18 is preferably about 1⅛ inch+/−⅛ inch, but can differ from this as desired, and particularly for different sized animals.

The angled section 16 of the bottom 10 on a preferred embodiment has, preferably centered, but not necessarily, another opening 22 for feeding a treatment gas into the mask 2. Preferably, the opening 22 is surrounded with a fitting 24, preferably with a tubular fitting 25 having threads or spaced apart ridges and valleys, corrugations or a knurled surface 26 for attaching a hose or tubing. Alternatively, the threads or ridges and valleys, or knurled portion 26 can be on the inside surface of the tubular fitting 25 as the purpose of the features 25 is to provide a gripping or securing function for a hose, hose fitting, or tubing (not shown) that is attached to the tubular fitting 25 for piping a gas, with or without, other treatment material into the mask 2. Preferably the tubular fitting 25 is integral with a flange section 27 that is integral with the angled section 16 in a radiused manner. Preferably, for molding convenience and/or for a more compatible shape for the animal's mouth and nose portions of the head, the front 6, the back 8 and the sides 4, 5 of the mask 2 are connected to the bottom 10 with optional curved sections 28, 30, 29, 31, 32, 33, 34 and 35 each of which is integral with the bottom 12 and the sides 4, 5, the front 6 and the back 8 of the mask 2. The angled section 16 is preferred, but optionally the entire bottom of the mask can be flat and will work, but the medicine will not flow as effectively to the animal's nose and the lower portion of the mask cannot be cleaned and/or sterilized as effectively. For a horse the interior diameter of the tubular fitting 25 is preferably about ¾ inch+/−⅛ inch, but can differ from this as desired, and particularly for different sized animals.

As will be seen in later figures, the top of the mask 2 is open to allow the entry of an animals mouth and nose portions of its head. As shown in FIG. 1, preferably centered horizontally on the sides 4 and 5 (not shown) and preferably at or near the top of the mask 2, are securement holders, e.g. strap holders 36 and 37 (not shown in FIG. 1), each having an opening 38 and 39 (not shown) therein to allow a strap (not shown) to pass through to secure the mask 2 onto the animal for respiratory treatment. An optional, thicker strip 40, preferably integral with the upper portion of the mask 2, extends around the top periphery of the mask 2 for purpose of stiffening the top portion of the mask 2 to better hold its shape during placement on the animal and treatment. The securement holders 36 (and 37 not shown) can be located at a plurality of places on the mask 2, preferably on its exterior, so long as it will allow securing the mask 2 to the animal to hold the securement straps, cord, etc. in a manner to cause no discomfort to the animal that will cause problems in giving respiratory treatment to the animal.

Figure 2:
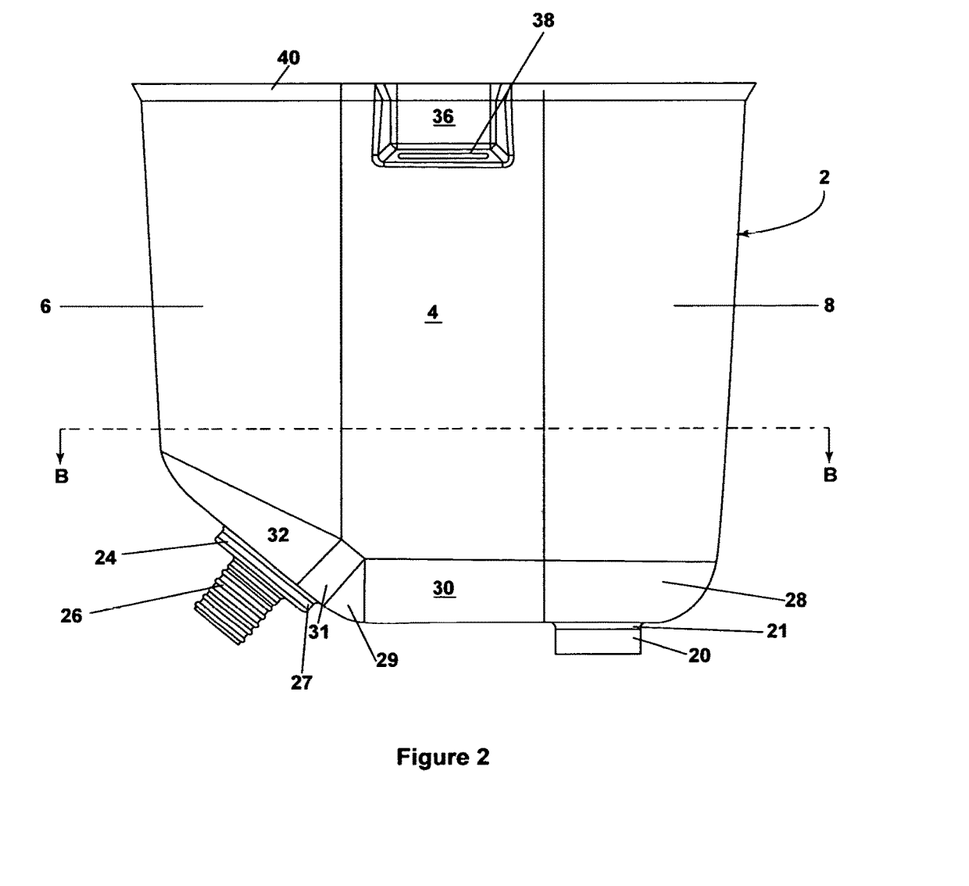
FIG. 2 is a side view of the respiratory mask shown in FIG. 1.
Figure 3:
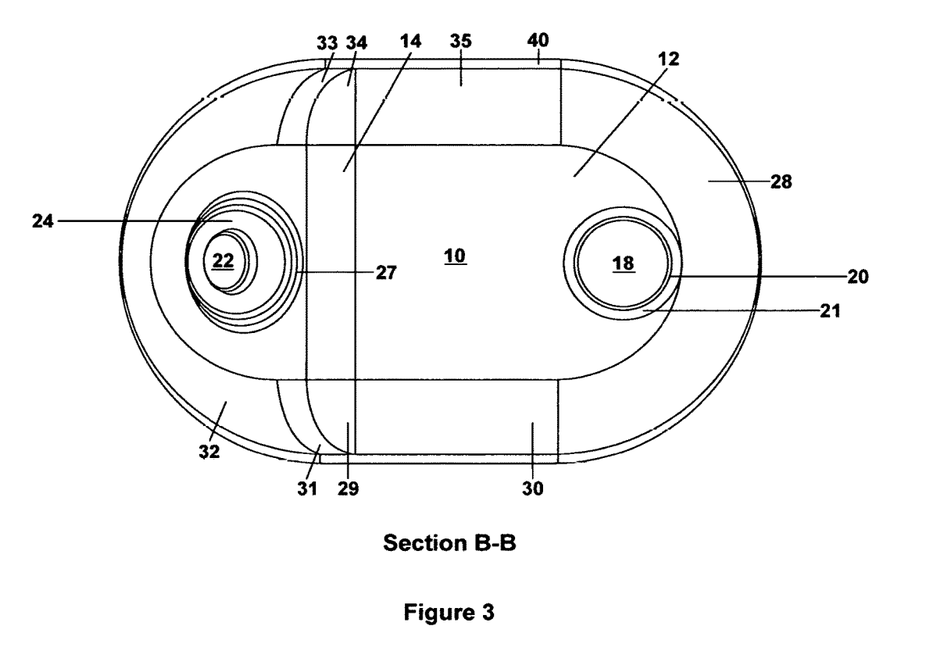
FIG. 3 is a cross sectional view along the plane B-B showing the inside bottom of the respiratory mask shown in FIG. 1.
Figure 4:
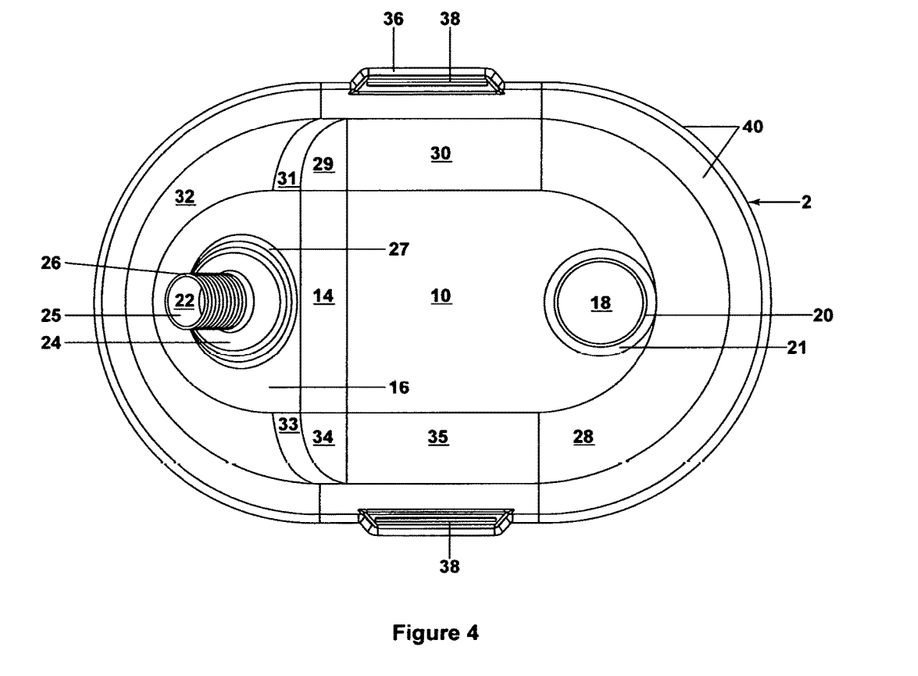
FIG. 4 is a bottom view looking up at the respiratory mask shown in FIG. 1.
Figure 5:
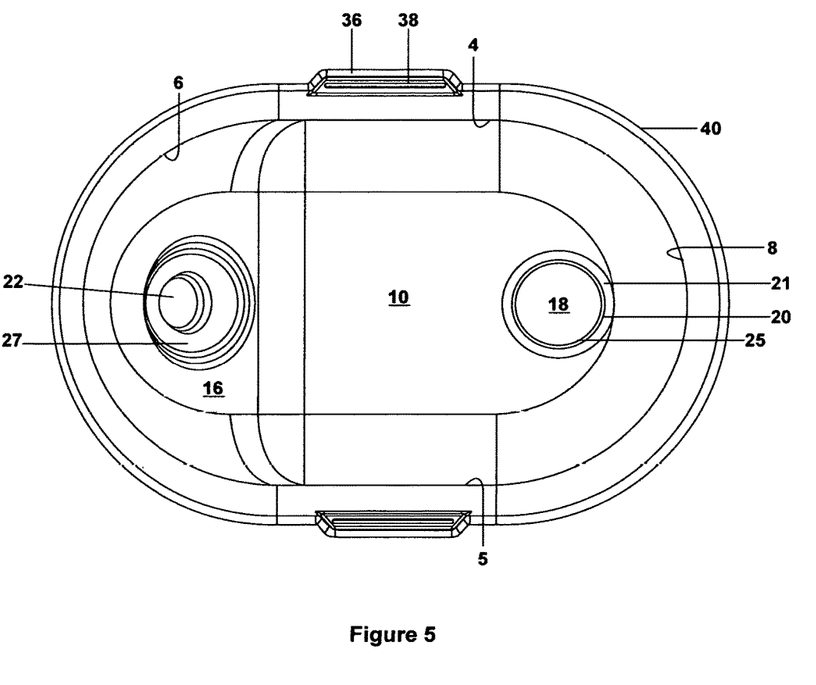
FIG. 5 is a plan view looking down [on] at the bottom of the respiratory mask shown in FIG. 1.

FIG. 2 is a side view of the mask 2 shown in FIG. 1. FIG. 3 is a plan view of the lower portion of the mask 2 in a cross-section taken along lines B-B shown in FIG. 2. FIG. 3 is a plan view taken at cross section B-B on FIG. 2 and shows the drain and air opening 18 with the curved transition 21 from the bottom wall 10 to form the fitting 20 clearly, and also shows a portion of the treating inlet opening 22 and the tops of the preferred fittings 20 and 24 respectively along with the flange 24 and flange side 27, the latter can be flat or stepped as shown, like side 20 on the drain 21. The openings 18 and 22 can be of various diameters, but the preferred interior diameters are 1⅛ inch for opening 18 and ¾ inch for opening 22. The I.D.'s of each of these openings can be substantially varied if desired as long as the desired drainage, air input and treatment input is satisfactory. The inlet hole 22 is separate from the drain hole 18 because of the debris that comes out of a horse's, or animal's nose or mouth, i.e. slobber, hay, dust, mucus, blood, needs a place to drain away from the mist that is coming into the mask for the horse to breathe. For example, FIG. 4 is a view looking at the bottom of the mask 2 and FIG. 5 is a plan view of the respiratory mask shown in FIG. 1. FIGS. 4 and 5 show the same components of the mask as earlier figures.

Figure 6:
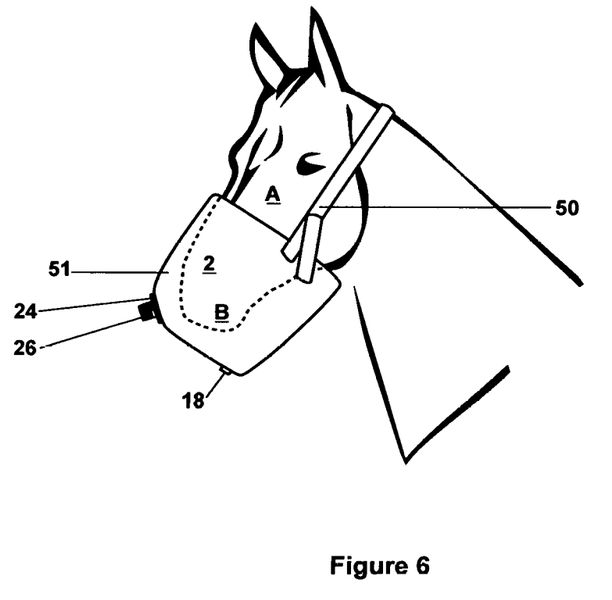
FIG. 6 is a perspective photograph view of the respiratory mask shown in FIG. 1 on a horse's head and held in place with straps or a strap according to the invention.
Figure 8:
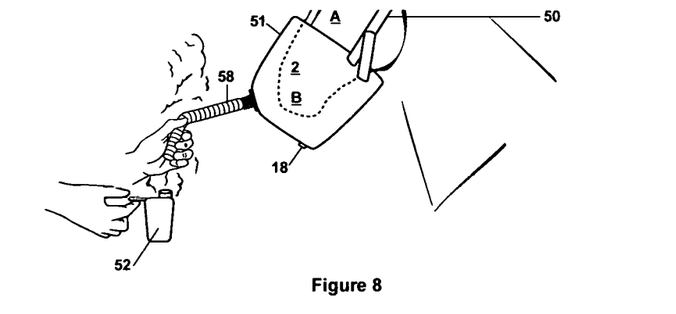
FIG. 8 is a partial similar view of FIG. 7 showing attaching the flexible corrugated tube to the medicine cup.
Figure 9:
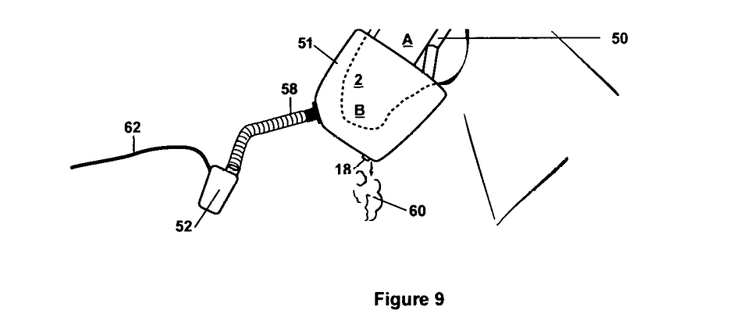
FIG. 9 is a partial side view of the mask on a horse with the medicine cup attached and feeding vapor to the inside of the mask and showing excess vapor exiting the drain in the bottom of the mask.
Figure 10:
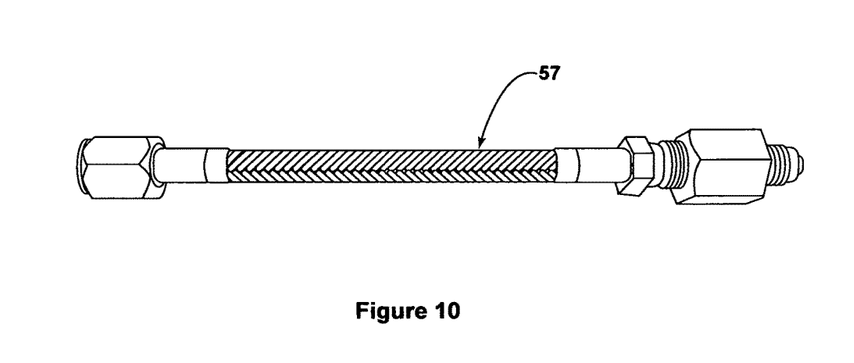
FIG. 10 is a perspective view of one kind of metal tubing preferred for use between a compressor and the medicine cup.

FIG. 6 is a perspective view of the respiratory mask 2 shown in FIGS. 1-5 on a horse's head A and held in place with straps or a strap 50 according to the invention. The drain opening 18 is at the bottom of the mask 2 for best drainage and the medicine inlet fitting 24,26 is close to the horse's nose B. The mask 2 is semi-transparent so you can see the end of the horse's nose 51 and mouth (also see FIG. 7), a side view of a horse wearing the mask 2 and a person's hand 53 holding a medicine cup 52 connected to a compressor 54 outlet 57 with a tube 62 to carry gas from the compressor 54 to the medicine cup 52 to produce a vapor 56 that will pass through a flexible tube 58 (see FIGS. 8 and 9 showing the medicine cup 52 being connected to the flexible tube 58 and after connection and during treatment of the horse). Note that FIG. 9 shows excess vapor 60 exiting through the drain opening 18. FIG. 10 is a plan view of a one type of metal flexible metal tubing 57 used between a compressor like the compressor 54 shown in FIG. 7, because of its ruggedness and its function as a heat sink and/or heat exchanger to lower the temperature of the conventional hot air coming from the air compressor 54 and a flexible polymer tubing 62 carrying the air stream to the medicine cup 52 (see FIG. 7. While this type of metal tube is preferred, it will be obvious to those skilled in the art that many different types of devices to reduce the temperature of the hot air coming from the air compressor 54 and the flexible tubing 62 can also be used to achieve the same functions.

The respiratory mask 2 of the invention can be made with any polymer that can be blow molded, usually a thermoplastic polymer and is preferably blow molded using a polymer of polyethylene and preferably high density polyethylene. One suitable polymer is DuPont's Surlyn® 1652, an ionomer of ethylene acid copolymer. To reduce cost, the thickness of the walls and bottom of the mask is very thin having a thickness in the range of 0.025 inch to 0.045 inch (0.635 mm-1.143 mm), or more, up to about 1.55 mm with a preferred thickness being 0.035 inch (0.889 mm). Other suitable polymers include, but are not limited to Surlyn® 8920 for extreme gloss and transparency, Surlyn® 1706 for enhanced chemical resistance Injection blow molding, Surlyn® 8528 and 1652 for additional flexibility and PC-100, PC-2000 and PC350 for glass-like transparency, easy of molding into complex shapes and BASF's SBC polymer, Styrolux™ and others suitable for blow molding.

The preferred respiratory mask of FIGS. 1-6 weighs about 4.0 ounces (wt.), about 113.5 grams, as shown in the figures, without the straps, and as used in the methods described above, but can weigh more such as 118, 123, 128 and up to 150 grams if desired. Using this technology and construction allows a respiratory mask to be made and sold at a price that is substantially less than half the price of other respiratory masks for the same kind of animals and same kind of treatment, e.g. this low weight makes the mask very low in manufacturing cost allowing a selling price substantially lower than competitive masks, such as about 50%, about 60% or about 70%, even up to about 80% lower than current competitive masks of this general type. It also provides much improved transparency to be able to see how the horse is breathing with its nose. One of the reasons for this disparity of cost is the much greater wall thickness of prior art masks, one having a thickness of about 0.094 inch (2.3876 mm) and a weight of about 1 pound 8 ounces, or 681 grams, with a selling price of more than 500%, and another weighing 1.2 pounds (about 544 grams) having a selling price that is more than 600%, of the selling price of the mask of the horse mask shown in FIGS. 1-5 of the invention.

Figure 11:
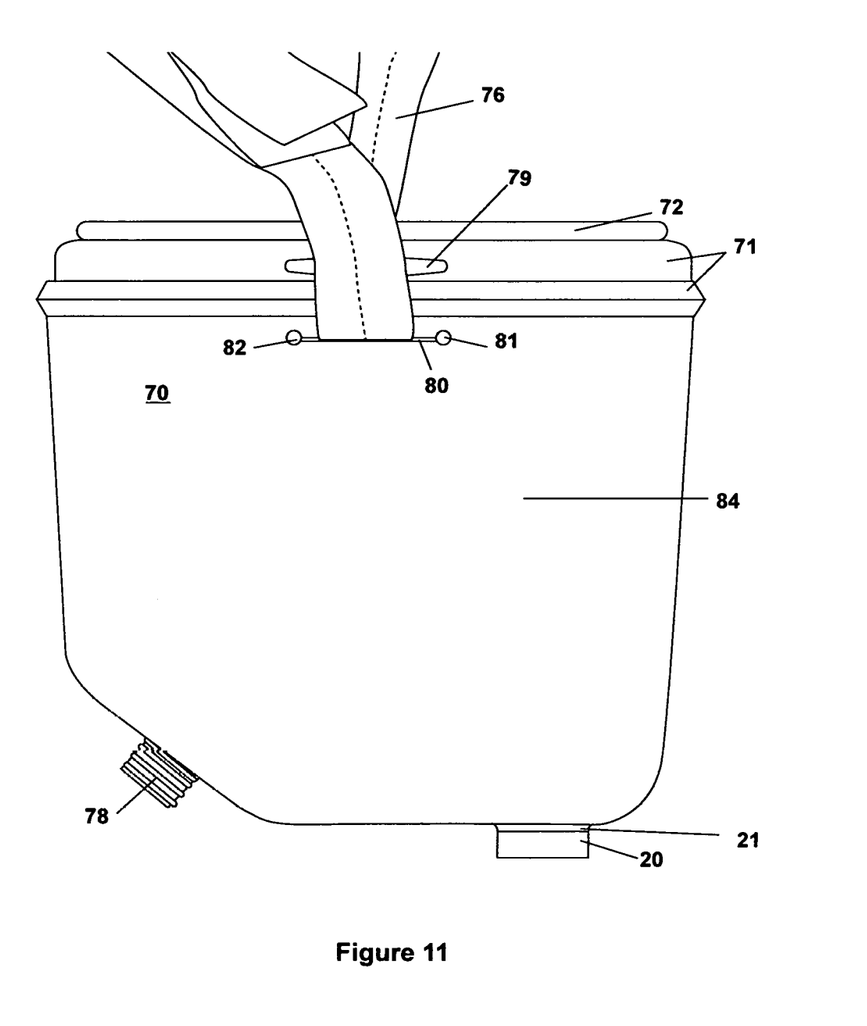
FIG. 11 is a side view of a different mask for equine colts.
Figure 12:
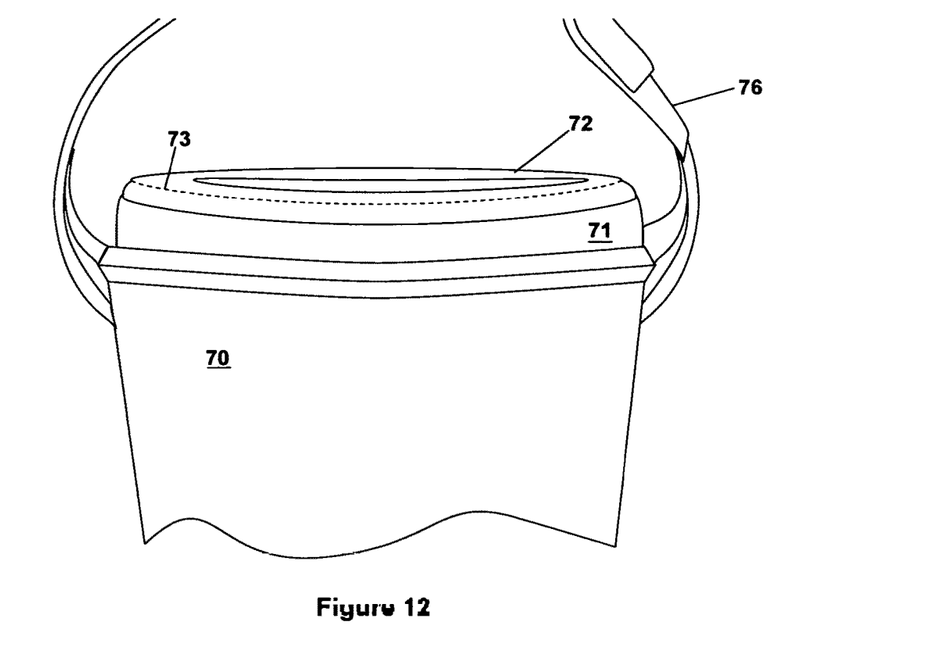
FIG. 12 is a partial front view of the mask of FIG. 11.
Figure 13:
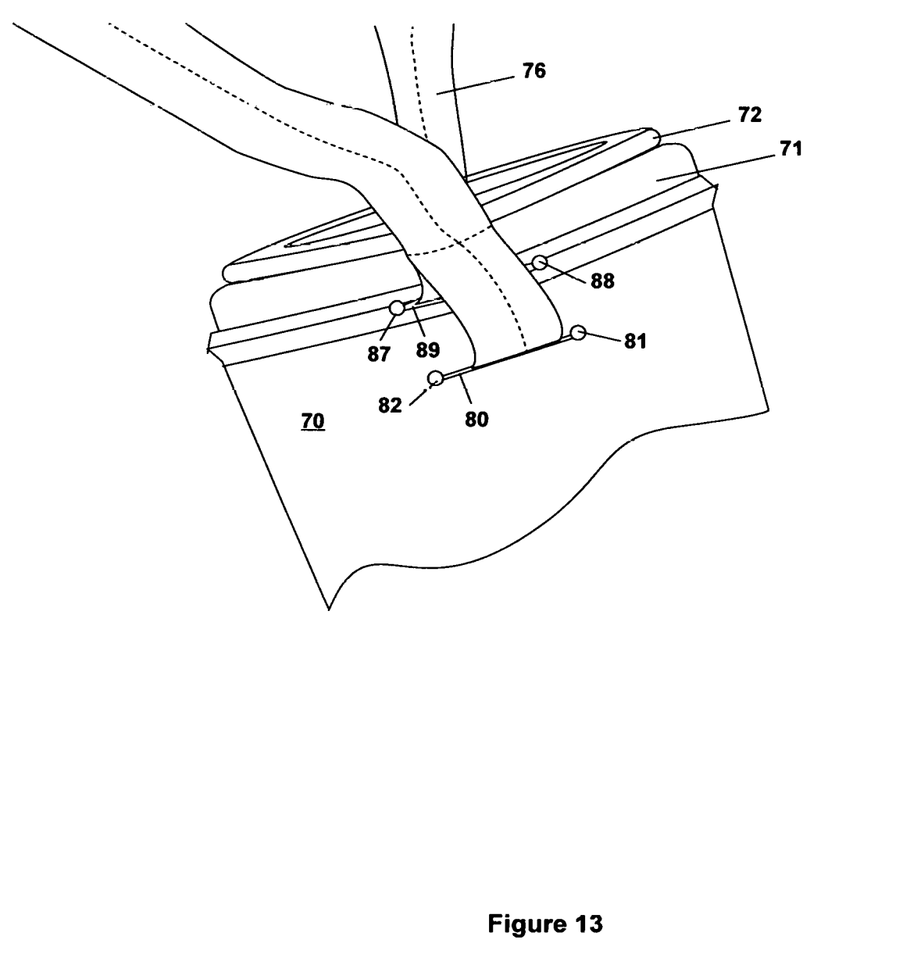
FIG. 13 is a perspective view of the mask of FIGS. 11 and 12.
Figure 14:
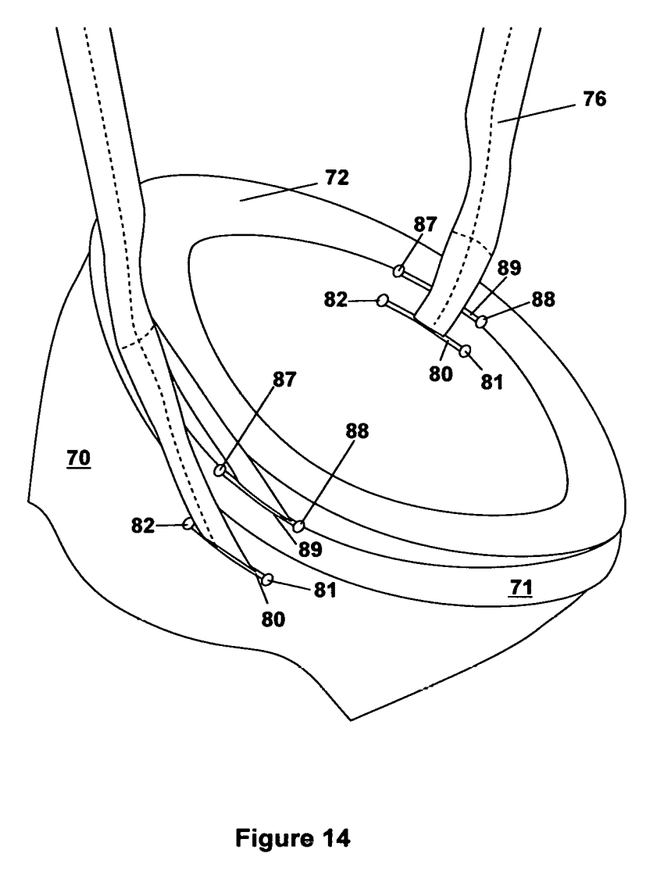
FIG. 14 is a different perspective view of the mask of FIGS. 11, 12 and 13.
Figure 15:
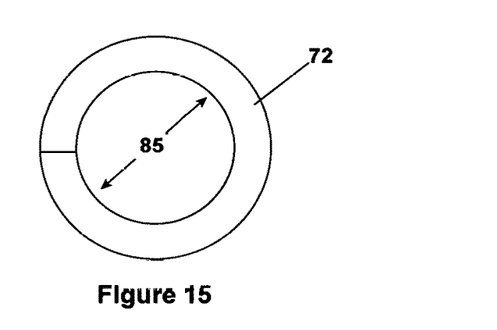
FIG. 15 is a plan view of a gasket used at the top of the mask of FIGS. 11-14.

The invention also includes masks for horse colts and other animals of similar size or smaller. This mask is formed in the same manner as the equine mask described above, but after forming the formed mask is modified as follows. FIG. 11 is a front view of another mask 70 of the invention, a mask for use on equine colts. This mask 70 is very similar to the mask 2 being longer than it is wide, the top being a wide oval, except for an additional extension portion 71 at the top of the colt mask 70 and a foam plastic ring gasket 72 around the inside of the very top of the extended top portion 71 of the colt mask 70. This foam plastic ring 72 is best seen in FIGS. 13, 14 and 15. Many foam plastics are suitable for making this ring 72 with a typical pipe insulation piece found in hardware stores being very economical. The piece of pipe insulation, one and one-half inches in outside diameter, for insulating a three quarter inch diameter pipe, is first cut to the proper length and is then fitted on a very top edge 73 of the extended top portion 71. The inside diameter 85 of the foam insulation 72 is about 0.75 inch. A preferred equine colt mask, having a different top portion than the equine mask shown in FIG. 2, etc., weighs 4.8 ounces alone and 5.1 ounces after the foam plastic ring 72 is installed. FIG. 15 shows the cross section of the foam insulation gasket ring used at the top of the colt mask 70. It is made from a length of foam plastic pipe insulation having a cross section measuring about 1.5 inch outside diameter and about ¾ inch inside diameter 85. The mask 70 is held onto the colt's head using strap(s) 76 like, or similar to, the straps 50 on the mask 2. The strap(s) 76 are attached to the colt mask 70 by passing through a slot opening 79 in the extended top portion 71, and/or a slit 80 between two starting holes 81,82 in an upper portion of both sides 84 of the colt mask 70. The insulation ring 72 is fitted onto the top portion 71 of the mask 4 as shown in FIGS. 11-14. The colt mask has a drain 78 and an inlet fitting 80, like the mask 2, for injection of gas and medicine vapor provided by the same equipment as used with mask 2. FIG. 12 is a partial end view of the colt mask 70 shown in FIG. 11. FIG. 13 is a side view of a slightly different colt mask 86, the difference from the colt mask 70 being that two holes 87,88 joined by a slit 89 located higher on the mask than the holes 81,82 and slit 80 replaces the slot 79 in the colt mask 70. The strap(s) 76 can pass through one or both of the slits 80 and/or 89 of the colt mask 86 as shown in a partial upper perspective view of the colt mask 86 in FIG. 14.

The method of the invention comprises the following steps:
1) Fill a medicine cup with 0.5-0.75 ounce of Silver Solution being careful to not over fill the medicine cup. Place the ring adapter on the out flow of the medicine cup. Silver Horse Care Solution is pure, nano-size silver particles in deionized 
water, an all-natural antimicrobial solution. It is safe for nebulizing horses and people.

2) Attach the corrugated tubing 58 (FIG. 7) to a mask, attach a plastic oxygen tube to an oxygen concentrator. When using an air compressor instead of oxygen concentrator, attach a tubing 57 (FIG. 7), preferably a metal tubing having good to high heat absorption, heat capacity, heat transfer coefficient and ability to dissipate heat to the air compressor and attach the other end to the medicine cup. Air compressors tend to heat the air to uncomfortable temperatures and the metal tubing will cool the air to a comfortable temperature for the horse/animal. A particularly good tubing is at least a 5 inch long, such as a six inch, preferably a seven inch long braided stainless steel covered plastic or metal tubing with metal couplings on each end (See FIG. 10), such as a braided hose available from HOSE MASTER Inc. as an RA1-AS S/S Braided Rubber Hose Assembly or similar metal hose. Various metal braded hoses of various types with crimped on brass or copper MNPT ends with female swivels attached to the hose with hose barbs or crimped seals.

3) Place mask on horse using the Velcro™ straps to hold the mask on the horse. Remember it may be scary to your horse at first. Let the horse look at it, smell it and be patient. After your horse is comfortable with the mask proceed to the following steps.

4) Attach the other end of the clear tubing to the inflow (small) spout of a medicine cup such as the medicine cup that is included with a MEDLINE Industries Inc. VixOne Nebulizer kit, or a similar med cup.

5) Turn on the compressor and make sure vapor is coming out of medicine cup.

6) Attach the medicine cup to the corrugated tubing 58 (FIG. 8) on the mask. Attach a ring adapter to the outflow spout of the medicine cup and slid it into the end of the flex hose. Use a small ring adapter to connect the flex hose, tubing 62 to the inlet spout of the medicine cup (See FIGS. 8 & 9).

7) Nebulize horse for approximately 15 minutes twice daily for 1st week then 3 or 4 times a week thereafter for maintenance. Allow the compressor to cool down before nebulizing the next horse. For cleaning the mask, spray with the disinfectant then rinse clean. Clean medicine cup after each use with mild soap or vinegar and water mix (like a coffee pot). It is recommended that the medicine cup and tubing be replaced every two weeks or as needed.

Regarding the metal cooling tube shown in FIG. 10, a heat sink and/or a heat exchanging tube or hose, the use of this device to cool the air coming from an air compressor not only prevents the animal from reacting to hot treatment vapor and ending the treatment prematurely as a result, it also solved another problem. Usually a flexible plastic tubing is used as the tubing 62 in FIG. 7 and it was slipped over a barbed hose nipple on the air compressor. The hot air coming from the air compressor would so soften the connecting end of the flexible plastic tubing that it would no longer be held in place by friction, would come loose with a loud “pop” noise scaring the animal, causing a premature end of the treatment or an undesired interruption. By attaching the metal braided hose shown in FIG. 10, or one like it except having a barbed nipple on its outlet end, this problem is avoided. This inventive feature in a treatment system is useful regardless of the type of animal mask being used. This solution to the problem is far superior to the prior art solution of putting a wire tie or zip tie around the tubing on the air compressor barbed nipple to prevent it from expanding, softening and slipping off of the barbed nipple. Another disadvantage of using the tie solution is a tendency, due to the cumbersome job of removing and replacing it each time, to leave it attached without cleaning the flexible tubing leading to contamination and re-infection of the animal. A preferred heat sink and/or heat exchanging metal hose or tubing is at least 5 inches long, one type being a Titeflex™ ¼ inch×5 inch OAL, R115-4 Teflon® lined stainless steel braid with stainless steel, brass or copper ¼ inch male NPT E/E and a SS, brass or copper female threaded fitting on the other end.

Different embodiments employing the concept and teachings of the invention will be apparent and obvious to those of ordinary skill in this art and these embodiments are likewise intended to be within the scope of the claims. The inventor does not intend to abandon any disclosed inventions that are reasonably disclosed but do not appear to be literally claimed below, but rather intends those embodiments to be included in the broad claims either literally or as equivalents to the embodiments that are literally included.

I claim:

1. A system for treating an animal with a respiratory mixture, the system comprising a mask for covering a nose, mouth and a portion of a head above the nose of an animal, the mask being made of a polymer and comprising walls integral with a bottom wall at a lower portion of the mask, the bottom wall having at least two openings, a first opening of the at least two openings being a drain and a second opening of the at least two openings spaced from the drain opening to allow a gaseous medicinal treatment mixture to enter the mask near the animals nose, the mask having a securement for holding the mask onto the animal, a medicine cup connected to the second opening, an air compressor and a heat sink and/or a heat exchanger to remove excess heat from the air stream coming from the air compressor between the air compressor and a hose or tubing leading to the medicine cup.

2. The system of claim 1 wherein the mask is made of a polyethylene and the location of the second opening being located closer to a top of the mask than the first opening, at least one wall of the mask having a thickness of less than about 1.143 mm.

3. The system of claim 1 wherein the mask is made of a flexible polymer, at least one wall of the mask having a thickness of less than about 1.143 millimeters, wherein the mask without said securement weighs no more than 150 grams.

4. The system of claim 1 wherein the bottom wall is comprised of a first portion and a second portion, a plane of the second portion forming an angle with a plane of the first portion, the first opening located in the second, angled portion and located closer to a top of the mask than the distance from the first opening in the first portion of the bottom wall of the mask to the top of the mask.

5. The system of claim 1 wherein the mask is for treating a colt or a similar size animal and has a foam gasket on and circling inner walls of a top portion of the mask.

6. The system of claim 1 wherein at least one wall has a thickness of about 0.9 mm or less.

7. The system of claim 1 wherein the mask is for a horse, a colt or a similar size animal and the mask weighs no more than 128 grams.

* * * * *